(12) United States Patent
Hataoka

(10) Patent No.: US 7,670,854 B2
(45) Date of Patent: Mar. 2, 2010

(54) IMMUNOLOGICAL ASSAY AND CHIP

(75) Inventor: Yukari Hataoka, Osaka (JP)

(73) Assignee: Panasonic Corporation, Osaka (JP)

( * ) Notice: Subject to any disclaimer, the term of this patent is extended or adjusted under 35 U.S.C. 154(b) by 222 days.

(21) Appl. No.: 11/905,648

(22) Filed: Oct. 3, 2007

(65) Prior Publication Data

US 2008/0312097 A1    Dec. 18, 2008

Related U.S. Application Data

(63) Continuation of application No. PCT/JP2007/057830, filed on Apr. 9, 2007.

(30) Foreign Application Priority Data

May 30, 2006   (JP)   .............................. 2006-149733

(51) Int. Cl.
*G01N 33/558* (2006.01)
(52) U.S. Cl. ...................................................... 436/514
(58) Field of Classification Search ....................... None
See application file for complete search history.

(56) References Cited

U.S. PATENT DOCUMENTS 5,458,852 A * 10/1995 Buechler ..................... 422/58
2003/0087325 A1   5/2003 Khayyami

FOREIGN PATENT DOCUMENTS

| JP | 2-62952 | 3/1990 |
| JP | 2001-4628 A | 1/2001 |
| JP | 2003-114229 A | 4/2003 |

OTHER PUBLICATIONS

International Preliminary Report on Patentability and Written Opinion of the International Searching Authority issued for International Patent Application No. PCT/JP2007/057830, mailed Dec. 24, 2008.
Barker, Susan L.R. et al., "Control of Flow Direction in Microfluidic Devices with Polyelectrolyte Multilayers," National Institute of Standards & Technology, Analytical Chemistry, Dec. 15, 2000, vol. 72, No. 24 p. 5925-5929.
Hisamoto, Hideaki et al., "On-Chip Integration of Sequential Ion-Sensing System Based on Intermittent Reagent Pumping and Formation of Two-Layer Flow," Analytical Chemistry, vol. 73, No. 22, Nov. 15, 2001, pp. 5551-5556.
Duffy David, et al., "Microfabricated Centrifugal Microfluidic Systems: Characterization and Multiple Enzymatic Assays," Analytical Chemistry, vol. 71, No. 20, Oct. 15, 1999, pp. 4669-4678.

* cited by examiner

*Primary Examiner*—Ann Y Lam
(74) *Attorney, Agent, or Firm*—McDermott Will & Emery LLP

(57) ABSTRACT

The present invention provides an immunological assay suitable to be carried out on a chip. After an antigen-antibody complex in which an antigen 2 to be measured and an antibody 3 have bound to each other was obtained in a reaction chamber 7, the amount of the antigen-antibody complex or the antibody that has not bound to the antigen to be measured by using a measurement solution obtained by using the sample solution 8 as a solvent. According to the present invention, the measurement solution for detecting the signal that reflects the amount of the substance to be measured can be obtained without using a buffer solution free from a substance to be measured, such as protein. Thus, it is not necessary to supply a buffer solution from the outside of the chip or to allow the buffer solution to be retained on the chip beforehand. Accordingly, an immunological assay can be carried out easily on a chip.

6 Claims, 8 Drawing Sheets

(1-A)

(1-B)

(1-C)

Removing (1-D)

Measurement (2-A)

(2-B)

(2-C)

Removing (2-D)

Measurement (Example)

(Reference Example)

IMMUNOLOGICAL ASSAY AND CHIP

This Application is a continuation of International Application Ser. No. PCT/JP2007/057830, whose international filing date is Apr. 9, 2007 which in turn claims the benefit of Japanese Patent Application No. 2006-149733, filed on May 30, 2006, the disclosures of which Applications are incorporated by reference herein. The benefit of the filing and priority dates of the International and Japanese Applications is respectfully requested.

TECHNICAL FIELD

The present invention relates to an immunological assay for measuring the amount of a specific component in a sample solution by using an antigen-antibody reaction, particularly an immunological assay suitable to be carried out on a chip. Furthermore, the present invention also relates to a chip suitable for carrying out the immunological assay.

BACKGROUND ART

Immunological assays are receiving attention as a method of identifying and quantitating, with high accuracy, proteins such as virus, bacteria, and allergenic substance contained in biological samples (for example, blood).

The immunological assay is roughly classified into an immunonephelometry and an immunolabeling assay. The immunonephelometry is a method of determining the change in turbidity of a sample solution that is caused by an antigen-antibody complex produced by an antigen-antibody reaction. The immunolabeling assay is a method of determining the change in the amount of a labeling substance after an antigen-antibody reaction by using an antibody labeled with the labeling substance.

The immunolabeling assay is subdivided according to the type of the labeling substance. Examples thereof include a radioimmunoassay in which a radioisotope is used as the labeling substance, an enzyme immunoassay (EIA) in which an enzyme is used, and a fluorescence immunoassay in which a fluorescent substance is used. In the EIA, as compared to other immunolabeling assays, the safety of the labeling substance is higher, it can be carried out by a simpler operation, and the measurement accuracy is higher. Therefore the EIA is used frequently.

A typical example of the EIA is an enzyme-linked immunosorbent assay (ELISA). An example of the ELISA is described with reference to FIG. 1.

<Step 1-A: Forming a Solid-Phase Antigen>

A solution containing a capture antigen having an epitope identical to that of an antigen to be measured is introduced into a reaction chamber 7 and is maintained at a predetermined temperature for a predetermined period of time, and thereby the capture antigen is allowed to adsorb to the surface of the reaction chamber 7. Thereafter the capture antigen to be allowed to adsorb is covered with protein that is not involved in a later antigen-antibody reaction and enzyme reaction (blocking). Thus a solid-phase antigen 6 is formed inside the reaction chamber 7. The solid-phase antigen 6 is being fixed to the surface of the reaction chamber 7 and therefore is not removed from the reaction chamber 7 by the washing described later.

<Step 1-B: Binding Reactions Between Antibody and Antigen to be Measured as Well as Solid-Phase Antigen>

An antibody 3 that specifically binds to an antigen to be measured 2 is added to a sample solution 9. The antibody 3 is being labeled with a labeling substance (an enzyme) 4. Thereafter, the sample solution 9 containing the antibody 3 is introduced into the reaction chamber 7. Thus, the antigen-antibody reaction proceeds between the antibody 3 and the antigen 2 to be measured as well as the solid-phase antigen 6 in the reaction chamber 7.

<Step 1-C: Removal of Unreacted Antibody and Antigen-Antibody Complex>

Using a wash solution, the inside of the reaction chamber 7 is washed. Thereby the antigen-antibody complex formed through binding of the antibody 3 to the antigen 2 to be measured and the antibody 3 that has not been bound to the solid-phase antigen 6 are removed from the reaction chamber 7. Accordingly, a conjugate of the solid-phase antigen 6 and the antibody 3 remains in the reaction chamber 7.

<Step 1-D: Measurement of the Amount of the Labeling Substance>

The amount of the labeling substance 4 of the conjugate of the solid-phase antigen 6 and the antibody 3 that has remained in the reaction chamber 7 is measured. This measurement is carried out, for example, as follows. First, a solution containing a measuring reagent (for example, a substrate of the enzyme) that reacts with the labeling substance 4 is prepared. The solution is prepared by adding the measuring reagent to a buffer solution typified by Tris-HCl buffer. Next, this solution is introduced into the reaction chamber 7, and thereby a measurement solution 10 is obtained that contains the measuring reagent and the conjugate of the solid-phase antigen 6 and the antibody 3. After the reaction between the measuring reagent and the labeling substance 4 is allowed to proceed in the measurement solution 10, a signal that reflects the amount of reaction product is detected.

As a result of this measurement, the amount of the antigen 2 to be measured in the sample solution 9 is calculated based on the amount of the solid-phase antigen 6 and the amount of the sample solution 9 introduced into the reaction chamber 7 in Step 1-B.

From the viewpoint of measuring the amount of the substance to be measured in the sample solution using a trace amount of sample solution in a short period of time, a chip-type biosensor is receiving attention. For example, JP 2 (1990)-062952 A discloses a chip-type biosensor including an insulating chip substrate, an electrode system disposed on the chip substrate, an enzyme reaction layer disposed on the electrode system, and an insulating layer that has notches and is disposed above the chip substrate in such a manner that the electrode system and the enzyme reaction layer are exposed. The enzyme reaction layer contains a measuring reagent for inducing an enzymatic cycling reaction, which is typified by an oxidoreductase and an electron mediator. An enzyme containing as a substrate the substance to be measured is used as the oxidoreductase. For example, glucose oxidase is used when the glucose amount is to be measured, and cholesterol oxidase is used when the cholesterol amount is to be measured. In this biosensor, a sample solution is dripped into the notches, so that the measuring reagent is dissolved in the sample solution. Thereby the reaction between the enzyme and the substance to be measured through an electron mediator (an enzymatic cycling reaction) proceeds. The amount of the substance to be measured in the sample solution is calculated based on the oxidation current value that is obtained by electrochemically oxidizing the electron mediator reduced by the enzyme reaction.

In the conventional immunological assay as shown in FIG. 1, as described above, Step 1-D is carried out using the measurement solution 10 containing a buffer solution as a solvent.

Accordingly, in order to carry out the immunological assay on a chip, it is necessary to supply the buffer solution from the outside of the chip or to allow the buffer solution to be retained on the chip beforehand. However, when the buffer solution is supplied from the outside of the chip, extra time and effort is required for the supply. When the buffer solution is allowed to be retained on the chip, this solution desirably is allowed to be retained on the chip in a hermetic state and in the state that facilitates it to be introduced into the reaction chamber for assaying while containing a component that reacts with the labeling substance. However, it is not easy to form such a retaining state on a chip.

DISCLOSURE OF INVENTION

The present invention is intended to provide an immunological assay that does not require a solvent of a measurement sample to be supplied from the outside of a chip or to have been retained on a chip beforehand and that is suitable for implementation on a chip. Furthermore, the present invention is intended to provide a chip that is suitable for the implementation of this immunological assay. The present invention also is intended to provide a measuring method using this chip.

Conventionally, in the immunological assay, it has been considered to be important to use, as a solvent of the measurement solution, a buffer solution free from the substance to be measured such as protein. Surprisingly, however, the present inventor found that a signal reflecting the amount of the substance to be measured also was detected even when a biological sample containing a substance to be measured such as protein was used as a solvent of the measurement solution instead of the buffer solution.

The present invention provides a method of measuring, using a chip, the amount of an antigen to be measured that is contained in a sample solution. The chip has a reaction chamber, a solvent retaining chamber, an effluent chamber, and an injection port for injecting the sample solution. The injection port and the reaction chamber are conneted to each other through a first channel. The injection port and the solvent retaining chamber are connected to each other through a second channel. The solvent retaining chamber and the reaction chamber are connected to each other through a third channel. The reaction chamber and the effluent chamber are connected to each other through a fourth channel. A measuring reagent is disposed between the injection port and the reaction chamber through the second channel, the solvent retaining chamber and the third channel. The method includes steps, in a following order, of injecting the sample solution from the injection port and dividing the sample solution into the reaction chamber and the solvent retaining chamber through the first channel and the second channel, respectively; obtaining an antigen-antibody complex by allowing an antigen to be measured that is contained in the sample solution to bind to an antibody that specifically binds to the antigen to be measured, in the reaction chamber; separating the antigen-antibody complex and the antibody that has not bound to the antigen to be measured from each other by transferring the sample solution in the reaction chamber to the effluent chamber through the fourth channel to leave one selected from: i) the antigen-antibody complex; and ii) the antibody that has not bound to the antigen to be measured, in the reaction chamber and to move the other into the effluent chamber; injecting, together with the measuring reagent, the sample solution retained in the solvent retaining chamber A1) into the reaction chamber through the third channel, or B1) into the effluent chamber through the third channel and the fourth channel; measuring the amount of the antibody that has not bound to the antigen to be measured or the antigen-antibody complex, either one of them that have been A2) remained in the reaction chamber, or B2) transferred to the effluent chamber; and calculating the amount of the antigen to be measured that is contained in the sample solution, from the amount measured in the step of measuring.

From another aspect, the present invention provides a method of measuring, using a chip, the amount of an antigen to be measured that is contained in a sample solution. The chip includes a reaction chamber, a solvent retaining chamber, an effluent chamber, and an injection port for injecting the sample solution. The injection port and the reaction chamber are connected to each other through a first channel. The injection port and the solvent retaining chamber are connected to each other through a second channel. The solvent retaining chamber and the effluent chamber are connected to each other through a third channel. The reaction chamber and the effluent chamber are connected to each other through a fourth channel. A measuring reagent is disposed between the injection port and the effluent chamber through the second channel, the solvent retaining chamber and the third channel. The method includes steps, in a following order, of: injecting the sample solution from the injection port and dividing the sample solution into the reaction chamber and the solvent retaining chamber through the first channel and the second channel, respectively; obtaining an antigen-antibody complex by allowing an antigen to be measured that is contained in the sample solution to bind to an antibody that specifically binds to the antigen to be measured, in the reaction chamber; separating the antigen-antibody complex and the antibody that has not bound to the antigen to be measured from each other by transferring the sample solution in the reaction chamber to the effluent chamber through the fourth channel to leave one selected from: i) the antigen-antibody complex; and ii) the antibody that has not bound to the antigen to be measured, in the reaction chamber and to move the other into the effluent chamber; injecting the sample solution retained in the solvent retaining chamber into the effluent chamber through the third channel together with the measuring reagent; measuring either one of them that the amount of the antibody that has not bound to the antigen to be measured and the amount of the antigen-antibody complex that have been transferred to the effluent chamber; and calculating the amount of the antigen to be measured that is contained in the sample solution, from the amount measured in the step of measuring.

From another aspect, the present invention provides a method of measuring the amount of an antigen to be measured that is contained in a sample solution. The method includes steps of obtaining an antigen-antibody complex by allowing the antigen to be measured to bind to an antibody that specifically binds to the antigen to be measured, in the reaction chamber; separating the antigen-antibody complex and the antibody that has not bound to the antigen to be measured; obtaining a measurement solution by adding the sample solution containing a measuring reagent to the antibody that has not bound to the antigen to be measured or to the antigen-antibody complex; measuring the amount of the antibody that has not bound to the antigen to be measured or the antigen-antibody complex, contained in the measurement solution; calculating the amount of the antigen to be measured that is contained in the sample solution, from the amount measured in the step of measuring.

From another aspect, the present invention provides a chip for measuring the amount of an antigen to be measured that is contained in a sample solution. The chip includes a reaction chamber, a solvent retaining chamber, an effluent chamber, and an injection port for injecting the sample solution. The injection port and the reaction chamber are connected to each other through a first channel. The injection port and the solvent retaining chamber are connected to each other through a second channel. The solvent retaining chamber and the reaction chamber are connected to each other through a third channel. The reaction chamber and the effluent chamber are connected to each other through a fourth channel. The sample solution injected from the injection port separates into the reaction chamber and the solvent retaining chamber through the first channel and the second channel, respectively. In the reaction chamber, the antigen to be measured is allowed to bind to an antibody that specifically binds to the antigen to be measured and thereby an antigen-antibody complex is obtained. The sample solution in the reaction chamber flows to the effluent chamber through the fourth channel, so that one selected from: i) the antigen-antibody complex; and ii) the antibody that has not bound to the antigen to be measured is left in the reaction chamber and the other moves into the effluent chamber, and thereby a separation of the antigen-antibody complex from the antibody that has not bound to the antigen to be measured is conducted. A measuring reagent is disposed between the injection port and the reaction chamber through the second channel, the solvent retaining chamber and the third channel. After the separation, the sample solution retained in the solvent retaining chamber is injected into the reaction chamber through the third channel together with the measuring reagent.

From another aspect, the present invention provides a chip for measuring the amount of an antigen to be measured that is contained in a sample solution. The chip includes a reaction chamber, a solvent retaining chamber, an effluent chamber, and an injection port for injecting the sample solution. The injection port and the reaction chamber are connected to each other through a first channel. The injection port and the solvent retaining chamber are connected to each other through a second channel. The solvent retaining chamber and the effluent chamber are connected to each other through a third channel. The reaction chamber and the effluent chamber are connected to each other through a fourth channel. The sample solution injected from the injection port separates into the reaction chamber and the solvent retaining chamber through the first channel and the second channel, respectively. In the reaction chamber, the antigen to be measured is allowed to bind to an antibody that specifically binds to the antigen to be measured and thereby an antigen-antibody complex is obtained. The sample solution in the reaction chamber flows to the effluent chamber through the fourth channel, so that one selected from: i) the antigen-antibody complex; and ii) the antibody that has not bound to the antigen to be measured is left in the reaction chamber and the other moves into the effluent chamber, and thereby a separation of the antigen-antibody complex from the antibody that has not bound to the antigen to be measured is conducted. A measuring reagent is disposed between the injection port and the effluent chamber through the second channel, the solvent retaining chamber and the third channel. After the separation, the sample solution retained in the solvent retaining chamber is injected into the effluent chamber through the third channel together with the measuring reagent.

According to the present invention, a sample solution for detecting a signal that reflects the amount of material to be measured can be obtained without using a buffer solution, when the immunological assay is performed, when the immunological assay is performed.

DESCRIPTION OF THE PREFERRED EMBODIMENTS

Figure 1:
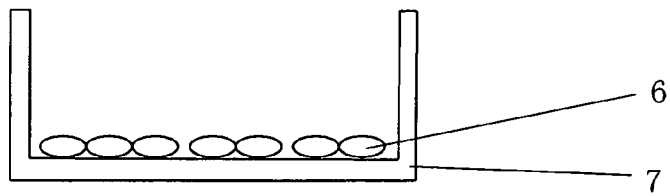
FIG. 1 is a flow chart for explaining one example of conventional immunological assays.
Figure 1:
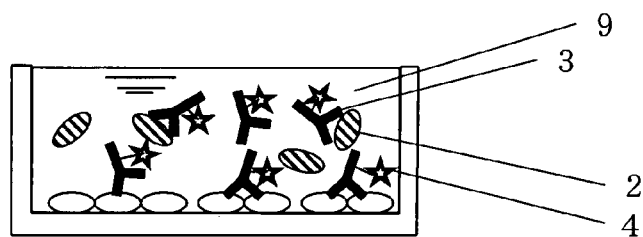
Figure 1:
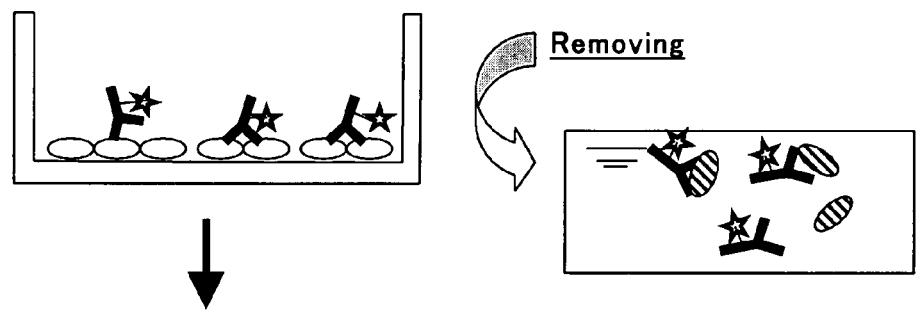
Figure 1:
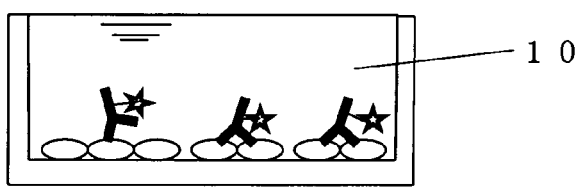
Figure 2:
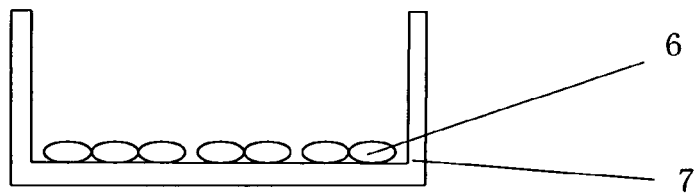
FIG. 2 is a flow chart for explaining one example of the immunological assays according to the present invention.
Figure 2:
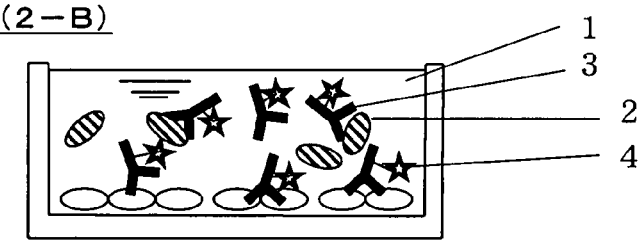
Figure 2:
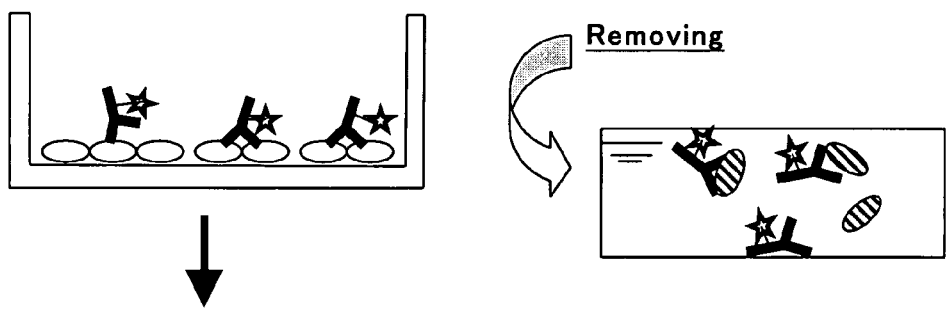
Figure 2:
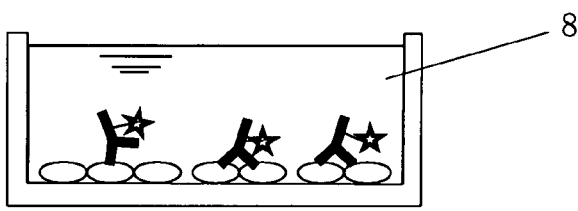

An example of the immunological assay according to the present invention is described with reference to the flow chart shown in FIG. 2.

<Step 2-A: Forming a Solid-Phase Antigen>

A solid-phase antigen 6 is formed by fixing a predetermined amount of capture antigen having an epitope identical to that of a specific protein (an antigen 2 to be measured) contained in a sample solution, to the surface of a reaction chamber 7. The fixation of the capture antigen can be carried out, for example, in the same manner as in Step 1-A employed in the conventional ELISA.

Examples of the material for the reaction chamber 7 include resins such as polystyrene, polyethylene terephthalate (PET), polycarbonate, and polydimethylsiloxane, glass, and magnetic materials. The reaction chamber 7 desirably has a shape capable of retaining a liquid, such as a tube type or a well type typified by a microplate.

<Step 2-B: Binding Step>

First, a predetermined amount of part 1 of the sample solution is dispensed. Examples of the sample solution include biological liquid samples such as blood, urine, saliva, sweat, and tear. Next, an antibody 3 labeled with a labeling substance 4 is added to the part 1 of the sample solution. The antibody 3 is a primary antibody that specifically binds to the antigen 2 to be measured. The other part 8 of the sample solution is reserved, with the antibody 3 being not added thereto. The antibody 3 can be a commercially available one or one prepared originally using a laboratory animal. The antibody 3 can be a polyclonal antibody but is preferably a monoclonal antibody from the viewpoint of improving the specificity and sensitivity of the antigen-antibody reaction. Example of the antigen 2 to be measured include proteins that is receiving high clinical attention, such as C-reactive protein (CRP), serum amyloid A, troponin T, creatine kinase MB, and retinol-binding protein. The labeling substance 4 is preferably an enzyme but can be a fluorescent dye or further a radioisotope.

The part 1 of the sample solution in the state immediately after the labeled antibody 3 is added thereto is introduced into the reaction chamber 7 to which the solid-phase antigen 6 has been fixed. With this operation, the part 1 of the sample solution is introduced into the reaction chamber 7. The part 1 of the sample solution after being introduced is maintained in the reaction chamber 7 at a predetermined temperature for a predetermined period of time. Thereby an antigen-antibody reaction proceeds competitively between the antibody 3 and the solid-phase antigen 6 as well as the antigen 2 to be measured, and an antigen-antibody complex that is a conjugate of the antigen 2 to be measured and the antibody 3 as well as a conjugate of the solid-phase antigen 6 and the antigen 3 are formed in the reaction chamber 7. Since the conjugate of the solid-phase antigen 6 and the antibody 3 has not bound to the antigen 2 to be measured, the conjugate is handled as "an antibody that has not bound to the antigen to be measured" as in the case of the antibody 3 in the present specification. As described above, the immunological assay of the present invention can be arranged as follows. That is, the solid-phase antigen is fixed to the reaction chamber and the antigen-antibody complex and the antibody that has not bound to the antigen to be measured, which has bound to the solid-phase antigen, are obtained in the binding step.

The antigen-antibody reaction that occurs in the reaction chamber 7 can be a noncompetitive reaction. The noncompetitive reaction can be obtained as follows. The part 1 of the sample solution to which the labeled antibody 3 has been added is maintained at a predetermined temperature for a predetermined period of time before being introduced into the reaction chamber 7. After the reaction between the antigen 2 to be measured and the labeled antibody 3 is allowed to reach a steady state, the part 1 of the sample solution is introduced into the reaction chamber 7. The antibody 3 that has not bound to the antigen 2 to be measured and the solid-phase antigen 6 are then allowed to react with each other. In this manner, the noncompetitive reaction can proceed. The temperature and period of time for allowing the antigen-antibody reaction to proceed can be set suitably according to the type of the antigen and antibody. The same applies to the following antigen-antibody reaction.

<Step 2-C: Separating Step>

The part 1 of the sample solution is removed from the reaction chamber 7 by using, for example, a pipette. According to this operation, the antigen-antibody complex is removed from the reaction chamber 7 while the antibody that has not bound to the antigen to be measured is left in the reaction chamber 7. Thus, the antigen-antibody complex and the antibody that has not bound to the antigen to be measured obtained in the binding step (Step 2-B) are separated. From the aspect of improving the accuracy of the separation, it is preferable to wash the reaction chamber with a wash solution typified by Tris-HCl buffer after removing the sample solution.

<Step 2-D: Measuring Step>

The amount of the labeling substance 4 in the antibody that has not bound to the antigen to be measured and that has remained in the reaction chamber 7 is measured. This measurement can be carried out, for example, as follows. First, a solution containing a measuring reagent is prepared. As a solvent of the solution, the other part 8 of the sample solution reserved in the binding step (Step 2-B) is used. The measuring reagent can be selected according to the type of the labeling substance 4. For instance, when the labeling substance 4 is an enzyme typified by alkaline phosphatase (ALP), it can be the substrate of the enzyme. Examples of a substrate of ALP include p-nitrophenylphosphate (pNPP). Subsequently, the solution is introduced into the reaction chamber 7, and thereby a measurement solution containing the measuring reagent and the antibody that has not bound to the antigen to be measured is obtained in the reaction chamber 7. Thus, the measurement solution is obtained by mixing the other part of the sample solution containing a measuring reagent that has been added after separating from the part of the sample solution and the antibody that has not bound to the antigen to be measured. Accordingly, the immunological assay of the present invention obtains the measurement solution, without using a buffer solution, by using the sample solution as a solvent. Thereafter, the amount of signal reflecting the amount of the reaction product is detected using, for example, a known optical measuring means or electrochemical measuring means after progressing the reaction between the measuring reagent and the labeling substance 4.

As mentioned above, conventionally, it has been considered to be important to use, as a solvent of the measurement solution, a buffer solution free from protein. This is intended to perform the measurement reaction without a material that inhibits the reaction. However, it seems that a measurement solution that can perform a good measurement can be prepared even when the sample solution is used as a solvent. Since as described later in Example, a signal reflecting the amount of the substance to be measured can be detected with excellent accuracy to an extent comparable to the case of using a buffer solution.

<Calculating Step>

Based on the amount (measurement result) measured in the measuring step, the amount of the antigen to be measured is calculated. More specifically, the amount of the antigen 2 to be measured is calculated based on the amount of the solid-phase antigen 6 that has been fixed to the reaction chamber 7 and the amount of the part 1 of the sample solution that was introduced into the reaction chamber in the binding step (Step 2-B) that are obtained as result of the measurement described above. The amount of the antigen to be measured can be expressed as a physical quantity that can be associated with the above-mentioned amount, for example, the concentration. Thus the amount of the antigen to be measured that is contained in the sample solution is calculated from the amount of the antibody that has not bound to the antigen to be measured or the amount of the antigen-antibody complex as described later, which has been measured in the measuring step.

Figure 8:
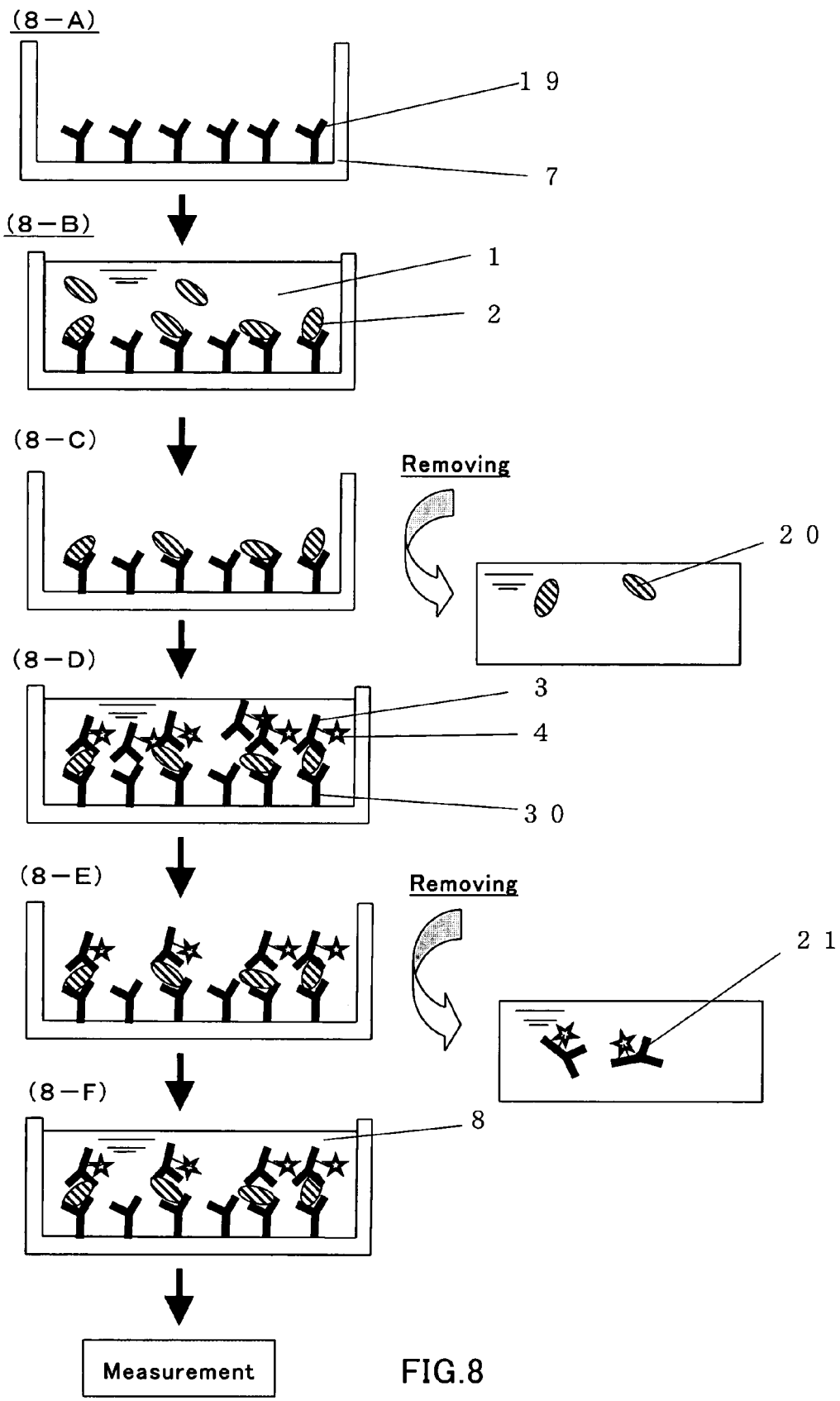
FIG. 8 is a flow chart for explaining one example in which an antigen-antibody reaction between an antibody and an antigen to be measured is performed by a sandwich method.

Another example of the immunological assay according to the present invention is described with reference to the step diagram shown in FIG. 8. In this example, the antigen-antibody reaction between an antibody and an antigen to be measured is carried out by the sandwich method.

<Step 8-A: Forming a Solid-Phase Antibody>

A predetermined amount of capture antibody to bind to an antigen 2 to be measured that is contained in a sample solution is fixed to the surface of the reaction chamber 7 and thereby a solid-phase antibody 19 is formed. The fixation of the capture antibody can be carried out, for example, in the same manner as in Step 2-A in the immunological assay shown in FIG. 2.

<Steps 8-B to 8-D: Binding Step>

A predetermined amount of sample solution is dispensed. Thus, a part 1 of the sample solution and the other part 8 of the sample solution are prepared.

The part 1 of the sample solution is introduced into the reaction chamber 7 to which the solid-phase antibody 19 has been fixed (Step 8-B). With this operation, the part 1 of the sample solution is introduced into the reaction chamber 7.

The part 1 of the sample solution thus introduced is maintained in the reaction chamber 7 at a predetermined temperature for a predetermined period of time. Thus, an antigen-antibody reaction proceeds between the solid-phase antibody 19 and the antigen 2 to be measured, and a conjugate of the antigen 2 to be measured and the solid-phase antibody 19 is formed in the reaction chamber 7.

Subsequently, the part 1 of the sample solution is removed from the reaction chamber 7 by using, for example, a pipette (Step 8-C). In this step, the antigen 2 to be measured that has not bound to the solid-phase antibody 19 is removed from the reaction chamber 7 while the conjugate of the antigen 2 to be measured and the solid-phase antibody 19 is left in the reaction chamber 7. From the aspect of removing absolutely the antigen 2 to be measured that has not bound to the solid-phase antibody 19 from the reaction chamber 7, the reaction chamber 7 is preferably washed by a wash solution typified by Tris-HCl buffer after removing the part 1 of the sample solution.

Thereafter, a solution 30 is introduced into the reaction chamber 7. The solution 30 is prepared by adding a predetermined amount of antibody 3 labeled with a labeling substance 4 to a solvent free from protein having an epitope identical to that of the antigen 2 to be measured. The antibody 3 to be used herein is a primary antibody that also can bind to the antigen 2 to be measured that has bound to the solid-phase antibody 19. An example of the solvent for the solution 30 is Tris-HCl buffer. The solution 30 introduced as described above is maintained in the reaction chamber 7 at a predetermined temperature for a predetermined period of time (Step 8-D). Thus, an antigen-antibody reaction proceeds between the labeled antibody 3 and the antigen 2 to be measured that has bound to the solid-phase antibody 19. This antigen-antibody reaction gives an antigen-antibody complex that is a conjugate of the solid-phase antibody 19, the antigen 2 to be measured and the antibody 3, as well as the antibody that has not bound to the antigen to be measured and that is the remainder 21 of the labeled antibody 3. The remainder 21 of the antibody 3 is present in the solution 30 in the state of being released from the surface of the reaction chamber 7.

The immunological assay of the present invention can be arranged as follows. That is, the solid-phase antibody is disposed in the reaction chamber, the solid-phase antibody and the antigen to be measured are allowed to bind to each other in the binding step, further a part of the antibody is allowed to bind to the antigen to be measured that has bound to the solid-phase antibody, and thereby an antigen-antibody complex that is a conjugate of the solid-phase antibody, the antigen to be measured and the above-mentioned part of the antibody, as well as the antibody that has not bound to the antigen to be measured and that is the remainder of the antibody are obtained.

<Step 8-E: Separating Step>

The solution 30 is removed from the reaction chamber 7 (Step 8-E). The removal can be carried out in the same manner as in Step 8-C. By this step, the antibody that has not bound to the antigen to be measured is removed from the reaction chamber 7 while the antigen-antibody complex is left in the reaction chamber 7. Thus, the antigen-antibody complex obtained in the Step 8-D and the antibody that has not bound to the antigen to be measured are separated from each other.

<Step 8-F: Measuring Step>

The amount of the labeling substance 4 in the antigen-antibody complex that has remained in the reaction chamber 7 is measured. This measurement can be carried out in the same manner as in Step 2-D in the immunological assay shown in FIG. 2. The measurement solution used in the measurement is obtained by using, as a solvent, the other part 8 reserved in Step 8-B. Thus, a measurement solution that enables good measurement can be obtained by using the sample solution as a solvent instead of using a buffer solution.

<Calculating Step>

Based on the amount (measurement result) measured in the measuring step, the amount of the antigen to be measured is calculated. More specifically, based on the measurement result, i.e. the amount of the solid-phase antibody 19 fixed to the reaction chamber 7 and the amount of the part 1 of the sample solution introduced into the reaction chamber 7 in the binding step (Step 8-B), the amount of the antigen 2 to be measured is calculated. The amount of the antigen to be measured can be expressed as a physical quantity that can be associated with the above-mentioned amount, for example, the concentration.

Figure 3:
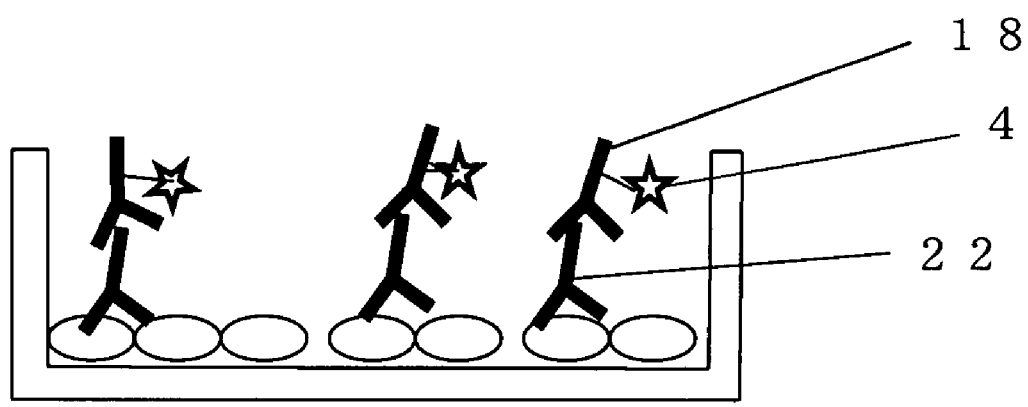
FIG. 3 is a diagram for explaining one example of the immunological assays according to the present invention that is carried out using an unlabeled primary antibody and a labeled secondary antibody.

In the immunological assay of the present invention, the operation and equipment to be used therein can be changed suitably as long as a signal reflecting the concentration of the substance to be measured can be detected to an extent comparable to the case of using a buffer solution as the solvent of the measurement solution. For example, in the immunological assays shown in FIGS. 2 and 8, the descriptions were made about the case where the primary antibody used for obtaining an antigen-antibody complex or an antibody that had not bound to an antigen to be measured was labeled with a labeling substance. Instead of this, however, as shown in the conceptual diagram in FIG. 3, a primary antibody 22 used for obtaining an antibody that has not bound to an antigen to be measured or an antigen-antibody complex is not labeled but a secondary antibody 18 that is allowed to bind to the unlabeled primary antibody 22 can be labeled with a labeling substance. Furthermore, in the immunological assays shown in FIGS. 2 and 8, the description was made about the case where the measuring step was carried out with respect to one selected from the antibody that had not bound to the antigen to be measured and the antigen-antibody complex, which remained in the reaction chamber 7 after the separating step. Instead of this, however, the measuring step can be carried out with respect to the other which has been removed from the reaction chamber 7 in the separating step. Furthermore, in the immunological assay of the present invention, as described above, from the viewpoint of facilitating the implementation on a chip, it is desirable to use as the reaction chamber a chip substrate having a shape capable of retaining a liquid that is typified by a microplate. However, it is not excluded to use, instead of this, a chip substrate having a shape that does not allow a liquid to be retained easily, which is typified by beads such as resin beads and magnetic beads. In the immunological assays shown in FIGS. 2 and 8, the descriptions were made about the case where the sample solution was dispensed and thereby the solution for inducing the antigen-antibody reaction in the reaction chamber and the solvent for preparing the measurement solution were prepared. Instead of this, however, a solvent for preparing the measurement solution can be prepared by newly collecting a sample solution.

Figure 4:
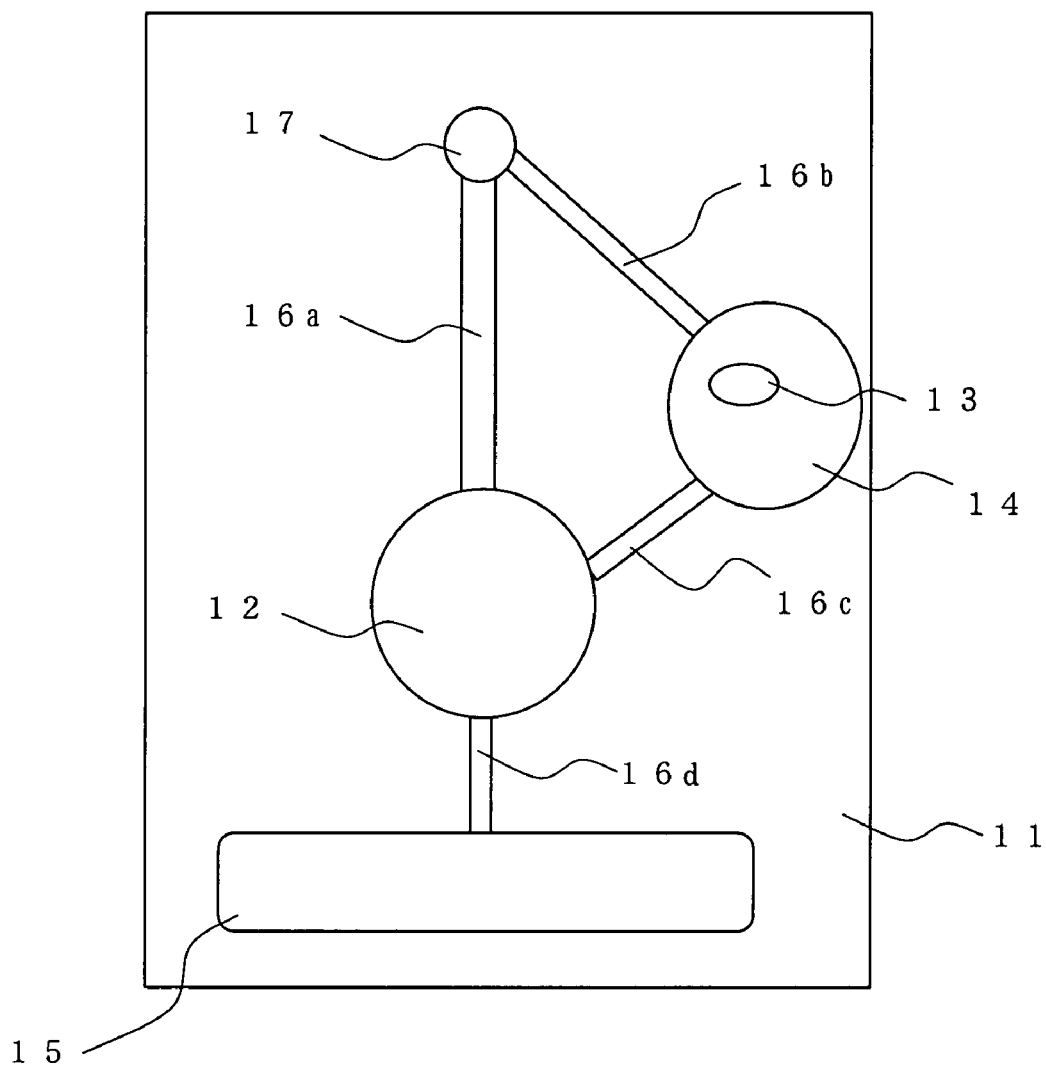
FIG. 4 is a diagram for explaining one example of the chips according to the present invention.

FIG. 4 is a diagram for explaining an example of the chip suitable for carrying out the immunological assay of the present invention.

The chip 100 includes: a chip substrate 11; and a reaction chamber 12, a solvent retaining chamber 14, an effluent chamber 15, and an injection port 17 through which a sample solution is injected, which are formed in the substrate 11. Examples of the material for the chip substrate 11 include materials for the reaction chamber 7 that are used in the immunological assays of the present invention, which is typified by PET.

The injection port 17 and the reaction chamber 12 are connected to each other through a channel 16a formed in the chip substrate 11. Furthermore, the injection port 17 and the solvent retaining chamber 14 are connected to each other through a channel 16b formed in the chip substrate 11. The channel 16a and the channel 16b are not in communication with each other. Accordingly, when a sample solution is injected into the injection port 17, the sample solution is divided to flow into the reaction chamber 12 and the chamber 14 through the channel 16a and the channel 16b, respectively. Thus, a part of the sample solution is sent to the reaction chamber 12 and the other part of the sample solution is sent to the solvent retaining chamber 14 and is retained in the chamber 14.

Figure 5:
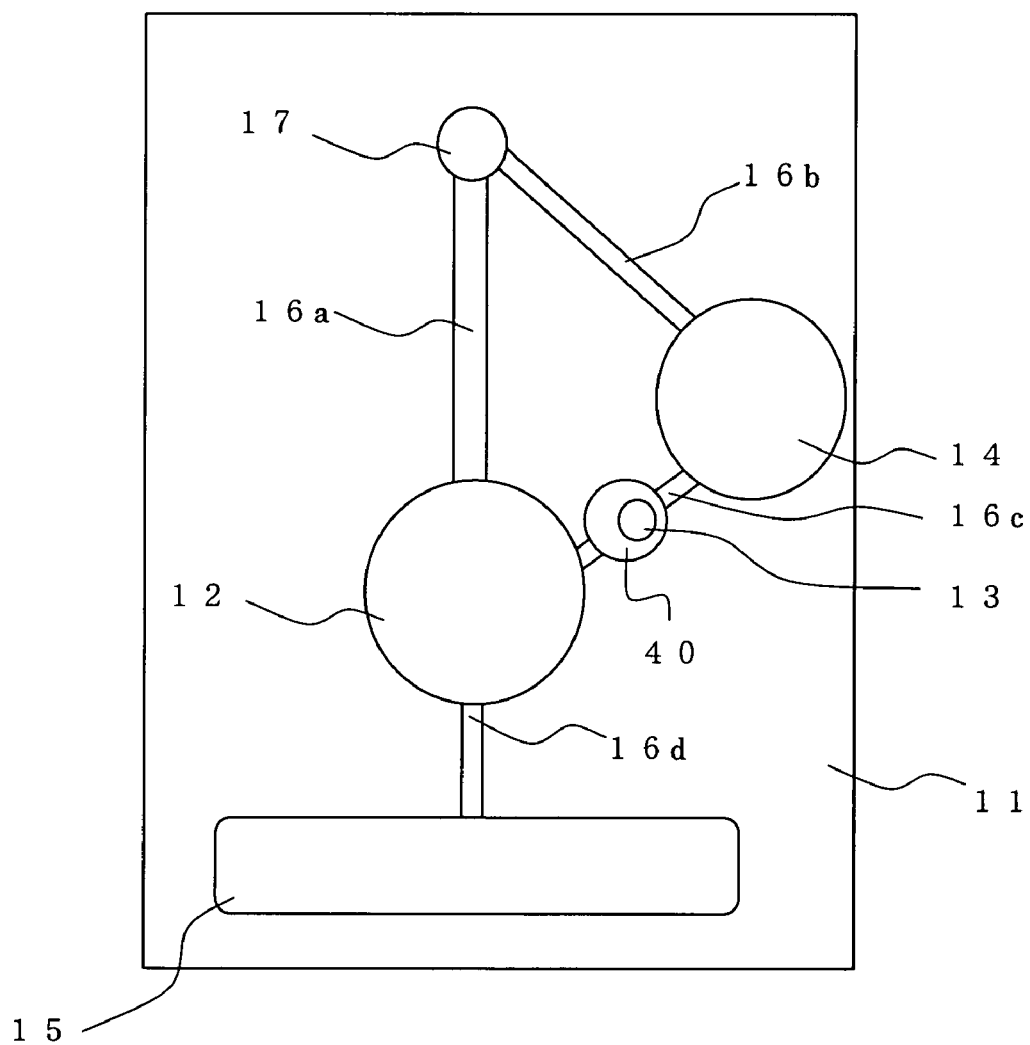
FIG. 5 is a diagram for explaining another example of the chips according to the present invention.

A measuring reagent 13 is disposed in the solvent retaining chamber 14. The measuring reagent 13 is a reagent for measuring the amount of the antibody that has not bound to the antigen to be measured or the amount of the antigen-antibody complex in the measurement solution as described in the description of the immunological assay of the present invention. The measuring reagent 13 is disposed so as to be solved in the solvent that is introduced into the solvent retaining chamber. Accordingly, when the above-mentioned other part of the sample solution is introduced into the solvent retaining chamber 14, the measuring reagent is added to the above-mentioned other part of the sample solution in the solvent retaining chamber 14. The measuring reagent 13 can be disposed in a condition soluble to the solvent by, for example, dropping a liquid reagent on the solvent retaining chamber 14 and drying. The measuring reagent 13 may be disposed on the path through which the above-mentioned other part of the sample solution passes until it is introduced into the solvent retaining chamber 14 (for example, the channel 16b). Furthermore, it may be disposed on the way between the solvent retaining chamber 14 and the reaction chamber 12. For example, the measuring reagent 13 may be disposed in a measuring reagent retaining chamber 40 formed by transforming the part of the channel 16c as the chip 101 shown in FIG. 5.

It is desirable that either one of (1) a solid-phase antigen and (2) a solid-phase antibody be fixed to the reaction chamber 12. It is desirable that a primary antibody that specifically binds to an antigen to be measured in the sample solution be placed inside the reaction chamber 12 or on the path through which the part of the sample solution passes until it is introduced into the reaction chamber 12, in the state of being able to be dissolved in the sample solution. The primary antibody is preferably in the state of having been labeled with a labeling substance. When the part of the sample solution is introduced into the reaction chamber 12, (1) an antigen-antibody complex that is a conjugate of the antigen to be measured and the antibody, as well as an antibody that has not bound to the antigen to be measured and that is a conjugate of a solid-phase antigen and the antibody are obtained in the case where the solid-phase antigen has been fixed to the reaction chamber 12, and (2) an antigen-antibody complex that is a conjugate of the solid-phase antibody, the antigen to be measured and the antibody, as well as an antibody that has not bound to the antigen to be measured and that is the remainder of the antibody are obtained in the case where the solid-phase antibody has been fixed to the reaction chamber 12.

The reaction chamber 12 and the effluent chamber 15 are connected to each other through a channel 16d formed in the chip substrate 11. The above-mentioned part of the sample solution is transferred from the reaction chamber 12 to the effluent chamber 15 through the channel 16d after the antigen-antibody reaction reaches the steady state in the reaction chamber 12. Accordingly, one selected from the antigen-antibody complex and the antibody that has not bound to the antigen to be measured is left in the reaction chamber 12 while the other moves into the effluent chamber 15. Thus, the antibody that has not bound to the antigen to be measured remains in the reaction chamber 12 in the case where the solid-phase antigen is placed in the reaction chamber 12, while the antigen-antibody complex remains in the reaction chamber 12 in the case where the solid-phase antibody is placed in the reaction chamber 12. Accordingly, the antigen-antibody complex and the antibody that has not bound to the antigen to be measured are separated from each other.

As described above, the chip of the present invention can be arranged as follows. That is, the solid-phase antigen is fixed to the reaction chamber, the antibody that has not bound to the antigen to be measured has bound to the solid-phase antigen, and, in the above-mentioned separation, the antibody that has not bound to the antigen to be measured is left in the reaction chamber while the antigen-antibody complex moves into the effluent chamber. Furthermore, as described above, in the chip of the present invention, the solid-phase antibody is fixed to the reaction chamber, the antigen-antibody complex is a conjugate of the solid-phase antibody, the antigen to be measured and the antibody, and, in the above-mentioned separation, the antigen-antibody complex is left in the reaction chamber while the antibody that has not bound to the antigen to be measured moves into the effluent chamber.

The sample solution retained in the solvent retaining chamber 14 (the above-mentioned other part) is injected into the reaction chamber 12 together with the measuring reagent 13 through the channel 16c after the above-mentioned separation. By this injection, a measurement solution containing the measuring reagent 13 and the above-mentioned one selected from the antigen-antibody complex and the antibody that has not bound to the antigen to be measured left in the reaction chamber 12 is obtained in the reaction chamber 12.

The solution can be sent through the respective channels by a known method of sending a solution, such as a method utilizing electroosmotic flow (for example, Barker et al., Anal. Chem.; (Article); 2000; 72(24); 5925-5929), a method utilizing injection force or suction power that is provided by a pump (for instance, Hisamoto et al., Anal. Chem.; (Article); 2001; 73(22); 5551-5556), and a method utilizing centrifugal force (for instance, Duffy et al., Anal. Chem.; (Article); 1999; 71(24); 4669-4678).

As described above, with the chip of the present invention, it is possible to obtain a measurement solution by using the sample solution as a solvent instead of using a buffer solution. As mentioned in the description of the immunological assay of the present invention, a signal reflecting the concentration of the substance to be measured can be detected by using the measurement solution with accuracy comparable to the case of using a buffer solution. The detection of the signal can be carried out with respect to the above-mentioned one left in the reaction chamber 12 or can be carried out with respect to the other moved to the effluent chamber 15. When the measuring step is carried out with respect to the other moved to the effluent chamber 15, the above-mentioned other part of the sample solution is not hold in the reaction chamber 12 and is moved into the effluent chamber 15 and thereby the measurement solution can be obtained in the effluent chamber 15. In this manner, the effluent chamber also can be used for implementation of an enzyme reaction in addition to effluent storage, and the intended use thereof is not limited by the term "effluent".

Figure 6:
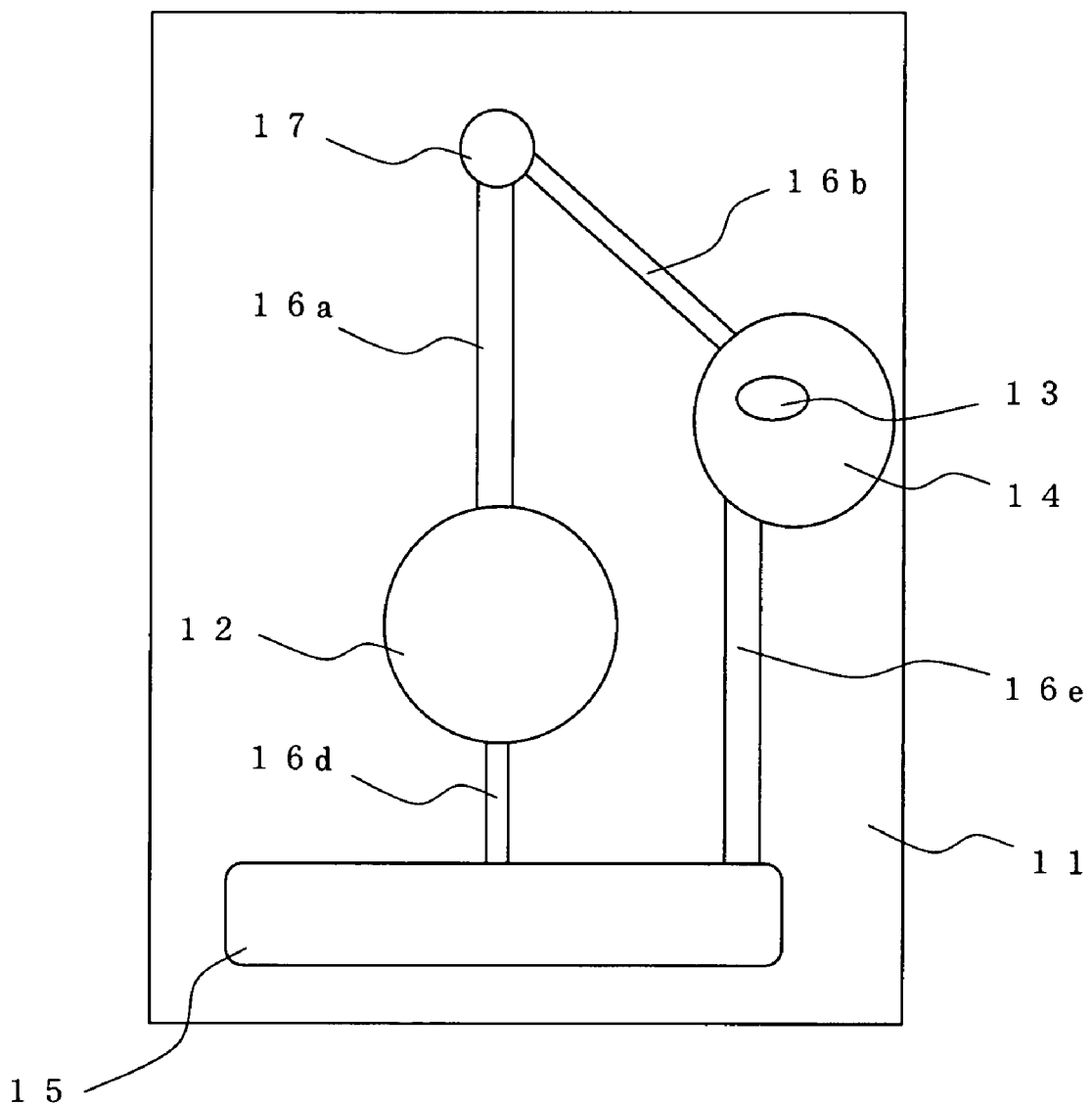
FIG. 6 is a diagram for explaining yet another example of the chips according to the present invention.

The chip of the present invention can be changed suitably in design as long as measurement can be carried out suitably well to an extent comparable to the case of using a buffer solution. For instance, another channel for introducing a labeled antibody into the reaction chamber can be formed additionally so that the antigen-antibody reaction can be implemented by the sandwich method. And for instance, as shown in FIG. 6, the chip of the present invention may be a chip 102 in which the measuring step is carried out only in the effluent chamber 15. The chip 102 has the same structure as the chip 100 except that a channel 16e connecting the solvent retaining chamber 14 and the effluent chamber 15 is formed, instead of the channel 16c, in the chip substrate 11. In the chip 102, the above-mentioned other part of the sample solution is injected into the effluent chamber 15 together with the measuring reagent 13 through the channel 16e without passing through the reaction chamber 12. In the chip 102, the measuring reagent 13 can be disposed on the path from the injection port 17 to the effluent chamber 15 through the channel 16b, the solvent retaining chamber 14 and the channel 16e.

Hereinafter, the present invention is described further in detail using examples.

REFERENCE EXAMPLE

First, a reference example is described in which an immunological assay was carried out by using a measurement solution whose solvent is a buffer solution.

[Production of Reaction Chamber]

A plurality of holes with a diameter of 5 mm were formed in a 1-mm thick PET sheet. After that, another PET sheet was attached to one surface of the above-mentioned PET sheet using a known light curing adhesive (LUXTRAK) so as to cover one ends of the holes. Thus a plurality of reaction chambers were produced.

[Fixation of CRP]

Using 50-mM Tris-HCl buffer (pH 7.5), a 42.3-nM CRP solution was prepared. 10 μl of the CRP solution was introduced into each of the respective reaction chambers. Subsequently, each reaction chamber was sealed with a resin sheet (a sheet for 96 holes). This was maintained at 35° C. for one hour and thereby the CRP was allowed to adsorb to the reaction chambers. Thereafter, the reaction chambers were washed with 50-mM Tris-HCl buffer (pH 7.5). Subsequently, 10 μl of blocking agent (manufactured by SEIKAGAKU CORPORATION, AppleDuo, CatNo. 200140) was added to each reaction chamber. This was maintained at 35° C. for one hour. Thus the CRP allowed to adsorb to the reaction chamber was blocked and a solid-phase antigen was formed in the reaction chamber. Thereafter, the reaction chambers were washed again with 50-mM Tris-HCl buffer (pH 7.5).

[Antigen-Antibody Reaction]

Sample solutions having a CRP concentration of 0 nM, 3.8 nM, 6.3 nM, 9.5 nM and 19 nM by adding CRP to serum (manufactured by SHINO-TEST CORPORATION, human control serum). Anti-CRP monoclonal antibody of 88 nM labeled with alkaline phosphatase (ALP) and the sample solution were introduced into the reaction chamber and maintained for 15 minutes at 35° C. Thus the antigen-antibody reactions between CRP/the solid-phase antigen and the antibody were allowed to proceed.

[Separating]

10 μl of 50-mM Tris-HCl buffer (pH 7.5) was introduced into the reaction chamber and then it was removed. Thereby the antigen-antibody complex that was a conjugate of CRP and the antibody was separated from the antibody that had not bound to the antigen to be measured and that was a conjugate of the solid-phase antigen and the antibody. More specifically, the antigen-antibody complex was removed from the reaction chamber, while the antibody that had not bound to the antigen to be measured was left in the reaction chambers.

[Measurement]

10 μl of p-nitrophenylphosphate solution (manufactured by Cygnus, PNPP Liquid Substrate, Cat No. F008-1000; pNPP) was introduced into each reaction chamber. Accordingly, a measurement solution was obtained in each reaction chamber. In the measurement solution, the enzyme reaction was allowed to proceed between pNPP and ALP of the antibody that had not bound to the antigen was allowed to proceed. After that, the absorbance of the product of the enzyme reaction, p-nitrophenol (pNP), was measured from each reaction chamber.

EXAMPLE

An immunological assay was carried out in the same manner as in the reference example except that a measurement solution obtained by using the sample solution as the solvent was used instead of pNPP and the amount of the products of the enzyme reaction is measured by an electrochemical method instead of the absorbance measurement.

The sample solution used as the solvent was prepared by dispensing the sample solution for inducing the antigen-antibody reaction.

A reagent for the enzymatic cycling reaction, which was made of potassium ferricyanide, diaphorase, NADP, malate dehydrogenase and sodium malate, was used as the measuring reagent.

The enzyme reaction was allowed to proceed by the following steps. First, 10 μl of the above-mentioned part of the sample solution to which the measuring reagent has been added was introduced to the reaction chamber to obtain the measurement solution. Next, the measurement solution was maintained in the reaction chamber for 7.5 minutes to allow the enzyme reaction to proceed. The amount of the product of the enzyme reaction was measured by measuring the current that was generated when a voltage of 400 mV was applied between the electrodes immersed in the measurement solution in the reaction chamber.

Figure 7:
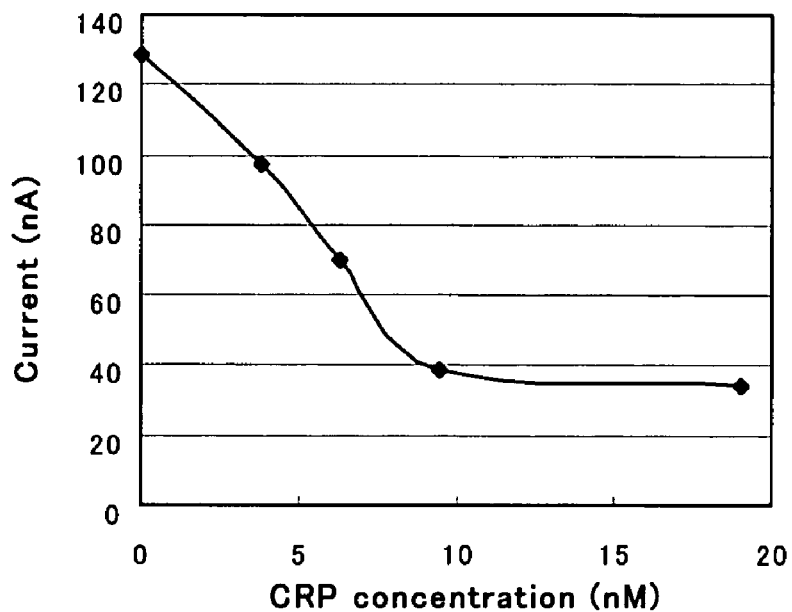
FIG. 7 is a graph showing the experimental results of Example and Reference Example.
Figure 7:
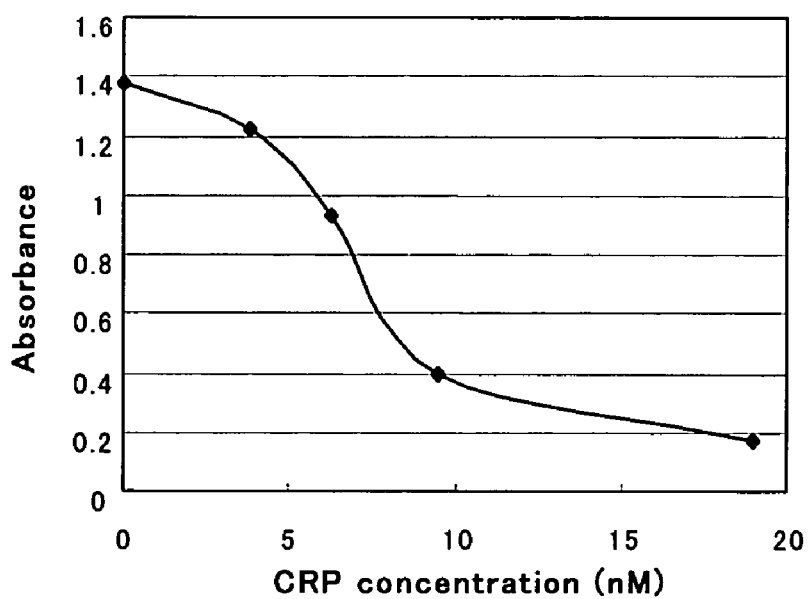

FIG. 7 is a graph showing the experimental results of Reference Example and Example. The absorbance was measured at 495 nm. As shown in FIG. 7, the absorbance and the current that reflected the difference of CRP concentration in the sample solutions were measured in both Examples. This showed that an immunological assay can be carried out with accuracy comparable to the case of using a buffer solution even when the sample solution was used as the solvent of the measurement solution.

INDUSTRIAL APPLICABILITY

The present invention provides an immunological assay in which a measurement solution for detecting the signal that reflects the amount of the substance to be measured can be obtained without using a buffer solution. Therefore, the present invention has a great deal of potential in each field where the immunological assay is required to be carried out on a chip.

What is claimed is:

1. A method of measuring, using a chip, the amount of an antigen to be measured that is contained in a sample solution,
wherein the chip comprises a reaction chamber, a solvent retaining chamber, an effluent chamber, and an injection port for injecting the sample solution,
the injection port and the reaction chamber are connected to each other through a first channel,
the injection port and the solvent retaining chamber are connected to each other through a second channel,
the solvent retaining chamber and the reaction chamber are connected to each other through a third channel,
the reaction chamber and the effluent chamber are connected to each other through a fourth channel,
a measuring reagent is disposed between the injection port and the reaction chamber, said measuring reagent being disposed in one of the second channel, the solvent retaining chamber and the third channel,
the method comprises steps, in a following order, of:
injecting the sample solution from the injection port and dividing the sample solution into the reaction chamber and the solvent retaining chamber through the first channel and the second channel, respectively;
obtaining an antigen-antibody complex by allowing an antigen to be measured that is contained in the sample solution to bind to an antibody that specifically binds to the antigen to be measured, in the reaction chamber;
separating the antigen-antibody complex and the antibody that has not bound to the antigen to be measured from each other by transferring the sample solution in the reaction chamber to the effluent chamber through the fourth channel to leave one selected from:
i) the antigen-antibody complex; and
ii) the antibody that has not bound to the antigen to be measured, in the reaction chamber and to move the other into the effluent chamber;
injecting, together with the measuring reagent, the sample solution retained in the solvent retaining chamber
A1) into the reaction chamber through the third channel, or
B1) into the effluent chamber through the third channel and the fourth channel;
measuring the amount of the antibody that has not bound to the antigen to be measured or the antigen-antibody complex, either one of them that have been
A2) remained in the reaction chamber, or
B2) transferred to the effluent chamber; and
calculating the amount of the antigen to be measured that is contained in the sample solution, from the amount measured in the step of measuring.

2. The method according to claim 1, wherein a solid-phase antigen has been fixed to the reaction chamber, the antibody that has not bound to the antigen to be measured has bound to the solid-phase antigen, and in the step of separating, the antibody that has not bound to the antigen to be measured is left in the reaction chamber while the antigen-antibody complex moves into the effluent chamber.

3. The method according to claim 1, wherein a solid-phase antibody has been fixed to the reaction chamber, the antigen-antibody complex is a conjugate of the solid-phase antibody, the antigen to be measured and the antibody, and in the step of separating, the antigen-antibody complex is left in the reaction chamber while the antibody that has not bound to the antigen to be measured moves into the effluent chamber.

4. A method of measuring, using a chip, the amount of an antigen to be measured that is contained in a sample solution,
wherein the chip comprises a reaction chamber, a solvent retaining chamber, an effluent chamber, and an injection port for injecting the sample solution,
the injection port and the reaction chamber are connected to each other through a first channel,
the injection port and the solvent retaining chamber are connected to each other through a second channel,
the solvent retaining chamber and the effluent chamber are connected to each other through a third channel,
the reaction chamber and the effluent chamber are connected to each other through a fourth channel,
a measuring reagent is disposed between the injection port and the effluent chamber said measuring reagent being disposed in one of the second channel, the solvent retaining chamber and the third channel,
the method comprises steps, in a following order, of:
injecting the sample solution from the injection port and dividing the sample solution into the reaction chamber and the solvent retaining chamber through the first channel and the second channel, respectively;
obtaining an antigen-antibody complex by allowing an antigen to be measured that is contained in the sample solution to bind to an antibody that specifically binds to the antigen to be measured, in the reaction chamber;
separating the antigen-antibody complex and the antibody that has not bound to the antigen to be measured from each other by transferring the sample solution in the reaction chamber to the effluent chamber through the fourth channel to leave one selected from:
i) the antigen-antibody complex; and
ii) the antibody that has not bound to the antigen to be measured, in the reaction chamber and to move the other into the effluent chamber;
injecting the sample solution retained in the solvent retaining chamber into the effluent chamber through the third channel together with the measuring reagent;
measuring either one of them that the amount of the antibody that has not bound to the antigen to be measured and the amount of the antigen-antibody complex that have been transferred to the effluent chamber; and
calculating the amount of the antigen to be measured that is contained in the sample solution, from the amount measured in the step of measuring.

5. The method according to claim 4, wherein a solid-phase antigen has been fixed to the reaction chamber, the antibody that has not bound to the antigen to be measured has bound to the solid-phase antigen, and in the step of separating, the antibody that has not bound to the antigen to be measured is left in the reaction chamber while the antigen-antibody complex moves into the effluent chamber.

6. The method according to claim 4, wherein a solid-phase antibody has been fixed to the reaction chamber, the antigen-antibody complex is a conjugate of the solid-phase antibody, the antigen to be measured and the antibody, and in the step of separating, the antigen-antibody complex is left in the reaction chamber while the antibody that has not bound to the antigen to be measured moves into the effluent chamber.

* * * * *

UNITED STATES PATENT AND TRADEMARK OFFICE
CERTIFICATE OF CORRECTION

PATENT NO. : 7,670,854 B2  Page 1 of 1
APPLICATION NO. : 11/905648
DATED : March 2, 2010
INVENTOR(S) : Yukari Hataoka It is certified that error appears in the above-identified patent and that said Letters Patent is hereby corrected as shown below:

In Column 16, Line 17 (Claim 4), change "chamber said" to --chamber, said--.

Signed and Sealed this

Twenty-fifth Day of May, 2010

David J. Kappos
*Director of the United States Patent and Trademark Office*